(12) United States Patent
Fisch

(10) Patent No.: US 11,666,540 B2
(45) Date of Patent: Jun. 6, 2023

(54) INDIVIDUALLY-PACKAGED WIPES FOR ENHANCING SEXUAL INTERCOURSE

(71) Applicant: ASPEN PARK PHARMACEUTICALS, INC., New York, NY (US)

(72) Inventor: Harry Fisch, New York, NY (US)

(73) Assignee: ROMAN HEALTH VENTURES, INC., New York City, NY (US)

(*) Notice: Subject to any disclaimer, the term of this patent is extended or adjusted under 35 U.S.C. 154(b) by 69 days.

(21) Appl. No.: 15/976,015

(22) Filed: May 10, 2018

(65) Prior Publication Data

US 2019/0046465 A1 Feb. 14, 2019

Related U.S. Application Data

(63) Continuation-in-part of application No. 15/114,620, filed as application No. PCT/US2015/011961 on Jan. 20, 2015, now abandoned.

(60) Provisional application No. 61/932,470, filed on Jan. 28, 2014.

(51) Int. Cl.
| | |
|---|---|
| *A61K 9/70* | (2006.01) |
| *A61K 31/167* | (2006.01) |
| *A61K 31/245* | (2006.01) |
| *A61P 15/10* | (2006.01) |

(52) U.S. Cl.
CPC .......... *A61K 9/7007* (2013.01); *A61K 31/167* (2013.01); *A61K 31/245* (2013.01); *A61P 15/10* (2018.01)

(58) Field of Classification Search
CPC .. A61K 9/7007; A61K 31/167; A61K 31/245; A61P 15/10
See application file for complete search history.

(56) References Cited

U.S. PATENT DOCUMENTS

| | | | | |
|---|---|---|---|---|
| 4,588,630 A | * | 5/1986 | Shimalla | D04H 1/56 |
| | | | | 15/209.1 |
| 2006/0029648 A1 | * | 2/2006 | Tsaur | A61K 9/0034 |
| | | | | 424/443 |

FOREIGN PATENT DOCUMENTS

GB 2420714 * 6/2007

OTHER PUBLICATIONS

DeNoon. CBS News [online]l 2008; downloaded from <URL https://www.cbsnews.com/news/erections-use-em-or-lose-em-07-07-2008/ > on Jun. 10, 2020; 3 pages. (Year: 2008).*
Anonymous. Male Health Center [online]; 2006; downloaded from <URL http://www.malehealthcenter.com/c_agingsex.html > on Jun. 10, 2020; 3 pages. (Year: 2006).*
McMahon, "Premature ejaculation"; Indian J. Urol., 23(2): 97-108 (2007).
Koskimaki, et al.; "Regular Intercourse Protects Against Erectile Dysfunction:Tampere Aging Male Urologic Study"; Amer. J. Med., 121(7): 592-596 (2008).
Freeman, "Erections: Use It or Lose It?", available on the website web.md.com, 2 pages, 2010.
Corty et al, "Canadian and American Sex Therapists' Perceptions of Normal and Abnormal Ejaculatory Latencies: How Long Should Intercourse Last", J. Sex Med 2008; 5; pp. 1251-1256.

* cited by examiner

*Primary Examiner* — David Browe
(74) *Attorney, Agent, or Firm* — Norris McLaughlin, P.A.

(57) ABSTRACT

The present invention relates to a sealed package containing one wipe, wherein the one wipe comprises a carrier and an active ingredient impregnated therein, wherein the active ingredient is selected from the group consisting of penile desensitizing agents. The sealed package can be opened, the wipe removed and wiped on the penis of a male to reduce the occurrence of premature ejaculation during subsequent intercourse. Repeated use of the wipes over time can result in statistically significant improvement in intravaginal ejaculatory latency time (IELT).

15 Claims, 2 Drawing Sheets

INDIVIDUALLY-PACKAGED WIPES FOR ENHANCING SEXUAL INTERCOURSE

PRIORITY CLAIM

This application is a continuation-in-part of U.S. Non-Provisional application Ser. No. 15/114,620, filed Jul. 27, 2016, which, in turn, is a 371 of International Patent Application No. PCT/US15/11961, filed Jan. 20, 2015, which, in turn, claims priority of U.S. Provisional Application Ser. No. 61/932,470, filed Jan. 28, 2014.

BACKGROUND OF THE INVENTION

1. Field of the Invention

The present invention relates to wipes for enhancing sexual intercourse and to methods of using the wipes to enhance a sexual encounter.

2. Description of Related Art

The American Urological Association defines premature ejaculation as ejaculation that occurs sooner than desired, either before or shortly after penetration, causing distress to either one or both partners (Guidelines on the Pharmacologic Management of Premature Ejaculation, American Urological Association, 2004). Premature ejaculation is among the most prevalent of male sexual complaints. A survey has estimated that premature ejaculation affects approximately 25% to 30% of men of all ages (see, Laumann et al., *JAMA*, 281: 537-544 (1999)). Persistent premature ejaculation can leave sexual partners feeling unsatisfied or unfulfilled, can cause stress or embarrassment to the affected male individual, and can lead to a deterioration of the intimate relationship between partners.

Treatments for premature ejaculation include application of topical anesthetics, e.g., preparations containing benzocaine or a lidocaine-prilocaine combination, to the penis to diminish sensitivity and delay ejaculation. However, these are typically sprayed and, if applied in the area where sexual intercourse is to occur, can leave the area wet and uncomfortable.

WO 2006/022683 describes stimulant/desensitizer swabs for use in stimulating erection and preventing premature ejaculation. A pharmaceutical composition including, for example, benzocaine or lidocaine as desensitizer is applied directly to the penis using a cotton swab. The stimulant will stimulate the penis to erection while the desensitizer will delay ejaculation. The applicator is cumbersome to use, not discrete at all, and, moreover, it takes time for the pharmaceutical composition to flow through the applicator to be available for application to the penis. Consistency in dosing is problematic.

There remains a need for means of reducing the incidence of premature ejaculation that are less cumbersome, more discrete and allow for instant application of the active ingredient to the penis.

SUMMARY OF THE INVENTION

These and other objects were met with the present invention, which relates in a first embodiment to a sealed package containing one wipe, said one wipe comprising a carrier and an active ingredient impregnated therein, wherein said active ingredient is selected from the group consisting of penile desensitizing agents.

The present invention relates in a second embodiment to a method of reducing the incidence of premature ejaculation in a male about to engage in sexual intercourse, the method comprising providing a sealed package according to the invention, wherein the sealed package comprises a carrier and a penile desensitizing agent impregnated therein, opening the package, removing the wipe from the package and wiping the wipe on the penis of said male.

The present invention relates in a third embodiment to a method of treating premature ejaculation in a male suffering therefrom, wherein premature ejaculation is defined as an average intravaginal ejaculatory latency time (IELT) of ≤2 minutes, said method comprising the following steps:

(a) opening a sealed package containing one wipe, said one wipe comprising a carrier and a penile desensitizing agent impregnated therein;

(b) removing the wipe from the package;

(c) wiping the wipe on the penis of said male in advance of an intravaginal encounter (penile penetration of the vagina);

(d) the male then engaging in said intravaginal encounter; and (e) repeating steps (a)-(c) in said male in advance of at least one subsequent intravaginal encounter;

(f) the male engaging in said at least one subsequent intravaginal encounter;

wherein as a result of performing steps (a)-(f) said male improves to exhibit an IELT of >2 minutes.

BRIEF DESCRIPTION OF THE DRAWINGS

The invention will now be described in greater detail with reference to the drawings, wherein.

DETAILED DESCRIPTION OF THE INVENTION

Figure 1:
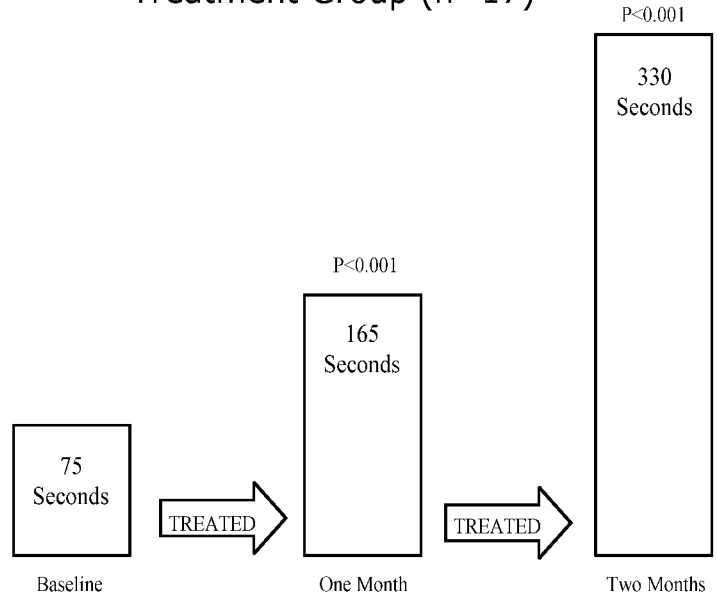
FIG. 1 is a graph summarizing the IELT results of the clinical study of Example 2 for the treatment group (n=17) for the study duration.

As used herein the phrase "containing one wipe" means that the sealed package contains exactly one wipe and no other wipes. Thus, the phrase is not met by a reference showing a sealed package containing multiple wipes unless each of the wipes is individually wrapped, in which case, the individual wrapping constitutes the "sealed package containing one wipe." A sealed package that contains multiple wipes, wherein each of the wipes is individually wrapped within its own individual sealed package, is within the present invention. Especially for carrying out the third embodiment of the invention, a sealed outer package, for example, made of paper or cardboard or any other suitable material, that contains within the sealed outer package multiple wipes, for example, 2, 3, 4, 5, 6, 7, 8, 9, 10 or more individual wipes, wherein each of the individual wipes is individually wrapped within its own individual sealed package, is especially suitable. Such a seal outer package containing multiple individually wrapped wipes within could advantageously also contain a set of instructions for use (or information about an information source, for example, a website, from which such instructions for use can be obtained), the instructions for use instructing the repeated and/or consistent/diligent use of the wipes during sexual encounters engaged in over a prolonged time of, for example, a week, two weeks, three weeks, a month, two months, three months, or even longer as a treatment for PE, or as a treatment for PE that may yield an improvement over time in IELT.

The phrase "penile desensitizing agent" means any chemical substance that when topically applied to the penis of a male who suffers from premature ejaculation delays but does not prevent ejaculation during subsequent sexual intercourse.

In one embodiment, the wipe comprises a penile desensitizing agent. Preferably, the penile desensitizing agent is selected from the group consisting of benzocaine, lidocaine and prilocaine. The concentration of the penile desensitizing agent in the wipes can vary, depending on the particular penile desensitizing agent and standards of practice in the art.

In a most preferred embodiment, the penile desensitizing agent is benzocaine.

In a second most preferred embodiment, the penile desensitizing agent is lidocaine.

In a third most preferred embodiment, the penile desensitizing agent is a combination of lidocaine and prilocaine.

In the most preferred embodiment, the penile desensitizing agent is benzocaine, which is in the wipe in a concentration of 3-7.5% in an inert water-soluble base, for example, water alone or in admixture with alcohols, for example, ethyl alcohol, or glycols, for example, propylene glycol. The amount of benzocaine solution employed in each individual wipe in one embodiment is a sufficient quantity to saturate, but not oversaturate the carrier.

In one embodiment, the wipe is not impregnated with any substance having an erection stimulating effect on the penis.

In one embodiment, the wipe consists of the carrier and the solution impregnated therein.

In one embodiment, the wipe consists of the carrier and the solution impregnated therein, and the solution consists of the penile desensitizing agent and inert ingredients, such as water, ethyl alcohol, propylene glycol, and the like, that neither desensitize the penis, nor stimulate the penis to erection.

In one embodiment, the wipe consists of the carrier and the solution impregnated therein, and the solution consists of benzocaine in a penile-desensitizing effective amount, for example, 3-7.5% by weight of the solution, and inert ingredients, such as water, ethyl alcohol, propylene glycol, and the like, that neither desensitize the penis, nor stimulate the penis to erection.

In another embodiment, the wipe is wiped on an already erect penis, particularly the head of an erect penis.

In another embodiment, the wipe is wiped on an already erect penis, particularly the head of an erect penis; and the wipe consists of the carrier and the solution impregnated therein, and the solution consists of the penile desensitizing agent and inert ingredients, such as water, ethyl alcohol, propylene glycol, and the like, that neither desensitize the penis, nor stimulate the penis to erection.

The carrier can be any suitable material. In one embodiment, the carrier is selected from the group consisting of paper and woven and nonwoven fabrics.

In a preferred embodiment, the carrier material is preferably a non-woven material, generally made of synthetic compounds. However, woven materials as well as the use of natural compounds in either woven or nonwoven materials are within the scope of the present invention. The texture and material of the wipe are of high relevance to the performance of the wipe. In one embodiment of the present invention the non-woven material comprises fibers selected from the group consisting of polyolefin, polyester, cellulose, rayon, polyamides, polyesteramide, polyvinyl alcohols, and combinations thereof. The substrate usable for this invention can be manufactured via any suitable process, such as but not limited to, spunlace process and preferably has a dry basis weight of between about 45 grams per square meter (gsm) and 100 gsm, more preferably between 45 gsm and 75 gsm.

In the most preferred embodiment, the carrier is a mixture of rayon and polyolefin, preferably polypropylene, and the penile desensitizing agent is benzocaine.

The packaging itself may be any suitable material, for example, paper, foils, or plastics, as well as any combination thereof, such as foil-lined paper, plastic-lined paper or a wax-lined paper. The package may take a variety of forms such as rectangular, oval, etc. The package may be provided with a separation structure, such as an edge tear area, a zipper-locked edge area, or an openable, adhesively sealed edge area.

Surprisingly, it has been found that consistent use by a male of wipes according to the present invention in advance of a series of intravaginal encounters conducted over time can result in a statistically significant improvement in the average intravaginal ejaculatory latency time (IELT) of said male. As defined herein, "premature ejaculation" means an average intravaginal ejaculatory latency time (IELT) of $\leq 2$ minutes. It has been found that repeated use by a male suffering PE, as evidenced by IELT of $\leq 2$ minutes, or $\leq 1.5$ minutes, or $\leq 1$ minutes, or $\leq 0.5$ minutes, of the inventive wipes over the course of time through multiple sexual encounters, each preferably separated by at least 24 hours, has the ability after a number of such sexual encounters, preferably at least 3, more preferably at least 5-10, occurring over a period of a week, or two weeks, or three weeks, or a month or more, has the ability to increase IELT in such male utilizing the wipes to the point that the male exhibits IELT of >2 minutes, preferably >3 minutes, most preferably >5 minutes, so that the male technically no longer meets the definition of suffering from PE.

Example 1

A male suffering frequent premature ejaculation is provided with a sealed package containing a wipe comprising a thermal bonded fabric carrier of 75% rayon and 25% polypropylene carrier, for example, Novonette Pattern #2, a thermal bonded fabric available from Ahlstrom Nonwoven LLC, Bethune, S.C., USA. The carrier is impregnated with a solution containing 4% benzocaine, water, ethyl alcohol and propylene glycol. Prior to sexual intercourse, the male opens the package, removes the wipe and wipes his penis with the wipe thereby topically transferring the benzocaine solution to his penis. During subsequent sexual intercourse, the benzocaine desensitizes the man's penis, prolonging the normal time for him between first penetration and ejaculation.

Example 2

In order to show additional advantages of benzocaine wipes, the following clinical studies were carried out in order to evaluate the efficacy, safety and tolerability of topically applied 4% benzocaine wipes in subjects with premature ejaculation (PE).

Twenty-six men over 18 years of age were enrolled in the studies.

Each of the men was required to be in a heterosexual, monogamous relationship, and suffer from PE, which, for the purposes of the studies, was defined as self-reported poor control over ejaculation, personal distress related to ejaculation, and average intravaginal ejaculatory latency time (IELT) ≤2 minutes on stopwatch measurement.

Subjects were randomized to two groups: (1) treatment group (n=17) (treatment with 4% benzocaine wipes) or (2) placebo group (n=9) (treatment with placebo wipes).

Subjects were given study medication sufficient for a month.

For the treatment group, the study medication consisted of individually wrapped packages containing a single wipe comprising a thermal bonded fabric carrier of 75% rayon and 25% polypropylene impregnated with a 4% benzocaine solution.

Benzocaine was the only therapeutic active ingredient in each wipe in the treatment group.

Each subject was instructed how to use the wipe and to use the study medication as much as he wanted in the next 1 month but to leave at least 24 hours between sexual encounters.

Each subject was also instructed for each sexual encounter to time his IELT with a stopwatch and to record his IELT time and tolerability data in a diary card.

At the end of Month 1, the diary card and any unused medication were collected, and the subject was asked to complete the Index of Premature Ejaculation (IPE) questionnaire.

At the end of Month 1, each subject was invited to continue the study in Month 2.

If the subject agreed to continue the study in Month 2, the subject was issued sufficient study medication and a new diary card.

At the end of Month 1, men in the placebo group were crossed over to the treatment group according to protocol.

At the end of Month 2, the diary card and any unused medication were again collected, and the subject was asked to complete the IPE questionnaire.

The primary objective desired was a change in IELT and IPE at two months.

Secondary outcomes desired included changes in questionnaire assessments, including global rating of distress, and medication assessment.

Results were recorded and compared at the end of Month 1 and Month 2.

Two-tailed T-test was used for comparison of all outcomes.

The IELT results returned at the end of Month 1 can be summarized as follows:

| Change in Duration Between Treatment and Placebo at 1 Month | | | | | | | |
|---|---|---|---|---|---|---|---|
| Group | Number of Enrollees | Sample Size | Mean (seconds) | Std Error | Std Dev | [95% Conf. Interval] | |
| Treatment | 17 | 86 | 164.80 | 11.40 | 106.00 | 142.09 | 187.56 |
| Placebo | 9 | 50 | 110.10 | 9.90 | 70.00 | 90.21 | 129.99 |
| Combined | 26 | 136 | 144.70 | 8.40 | 97.70 | 128.10 | 161.30 |
| Difference | | | 54.7 | 16.80 | | 21.50 | 87.90 |

Ha: diff > 0: Pr(T > t) = 0.007

The IELT results returned at the end of Month 2 can be summarized as follows:

| Change in Duration Between Treatment and Placebo at 2 Months | | | | | | | |
|---|---|---|---|---|---|---|---|
| Group | Number of Enrollees | Sample Size | Mean (seconds) | Std Error | Std Dev | [95% Conf. Interval] | |
| Treatment | 17 | 94 | 329.70 | 21.37 | 207.20 | 287.26 | 372.14 |
| Placebo | 9 | 50 | 110.10 | 9.90 | 70.00 | 90.21 | 129.99 |
| Difference | | | 219.6 | 23.55 | | 172.99 | 266.21 |

Ha: diff > 0: Pr(T > t) = 0.001

A graph summarizing the IELT results for the treatment group (n=17) for the study duration is shown in FIG. 1.

Figure 2:
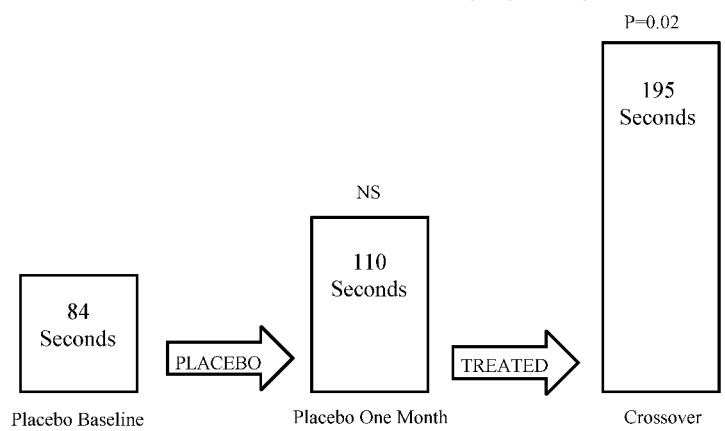
FIG. 2 is a graph summarizing the IELT results of the clinical study of Example 2 for the placebo/crossover group (n=9) for the study duration.

A graph summarizing the IELT results for the placebo/crossover group (n=9) for the study duration is shown in FIG. 2.

The IELT results are statistically significant and clinically meaningful.

The IELT results show a statistically significant improvement in IELT at Month 1 in the treatment group (165 seconds 2.75 minutes) compared to placebo (110 seconds 1.8 minutes).

The IELT results show the improvement was not static, but actually increased month-over-month, as the statistically significant improvement in IELT at Month 2 in the treatment group (330 seconds 5.5 minutes) reflects a doubling of ejaculatory time of the average man undergoing treatment by the end of Month 2 compared to Month 1.

Those men who initially were given placebo wipes, but were then crossed over to the treatment group after the first month, showed statistically significant improvement post-crossover (195 seconds 3.25 minutes).

Indeed, after 2 months, 82% of the men had IELT of >2 minutes and were no longer considered to have PE while under treatment.

One would not have expected the use of the wipes to have a cumulative effect on the ejaculatory time of the user over time, or that the ejaculatory time would increase so quickly to the point that the user would technically no longer be considered to suffer PE while under treatment.

The secondary outcomes were significant and meaningful as well.

The Index of Premature Ejaculation (IPE) Questionnaire assessment before and after treatment sought subjective responses in ten key indicators: (1) control over ejaculation; (2) confidence when ejaculated; (3) satisfaction frequency; (4) sense of control; (5) length of intercourse; (6) sexual satisfaction; (7) sexual relationship with partner; (8) sexual pleasure; (9) frustration with time to ejaculation; and (10) frustration with control over ejaculation.

Figure 3:
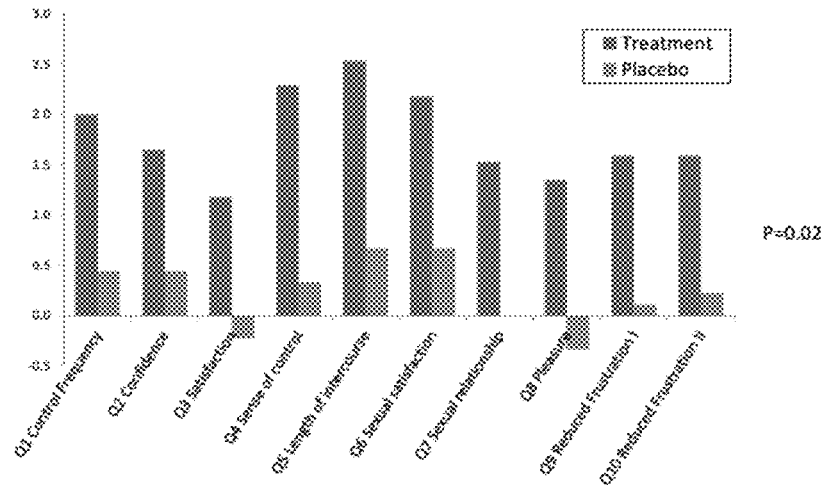
FIG. 3 is a graph summarizing the change in IPE (Index of Premature Ejaculation) for the treatment group in the clinical study of Example 2.

The change in IPE for the treatment group is graphically summarized in FIG. 3.

Figure 4:
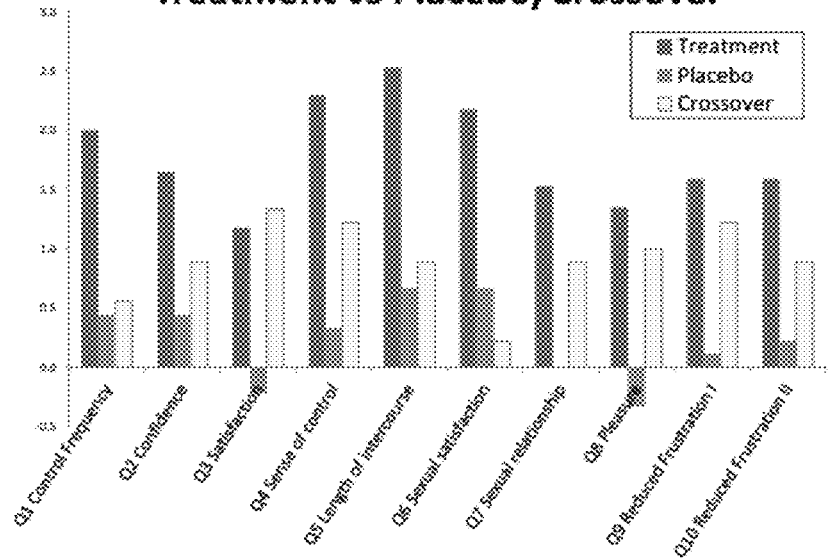
FIG. 4 is a graph summarizing the change in IPE for the placebo/crossover group in the clinical study of Example 2.

The change in IPE for the placebo/crossover group is graphically summarized in FIG. 4.

Clearly, the benefit was not only physical, as proven by the objective measurement of IELT, but also supported by patient-reported outcomes as measured by IPE.

The men undergoing treatment clearly felt greater sexual satisfaction and more confident and less frustrated while using the 4% benzocaine wipes.

Also, no transference to partners was reported.

While the present invention has been described in conjunction with the specific embodiments set forth above, many alternatives, modifications and other variations thereof

What is claimed is:

1. A method of treating premature ejaculation in a male suffering therefrom, wherein premature ejaculation is defined as an average intravaginal ejaculatory latency time (IELT) of <2 minutes, said method comprising the following steps:
   (a) opening a sealed package containing one wipe, wherein said wipe comprises a carrier and benzocaine impregnated therein, but wherein said wipe does not comprise any substance having an erection stimulating effect on the penis;
   (b) removing the wipe from the package;
   (c) wiping the wipe on the penis of said male in advance of an intravaginal encounter;
   (d) repeating steps (a)-(c) in said male in advance of each one of multiple subsequent intravaginal encounters occurring after said intravaginal encounter, each one of said multiple subsequent intravaginal encounters being separated from said intravaginal encounter and every other one of said multiple subsequent intravaginal encounters by at least 24 hours, said multiple subsequent intravaginal encounters amounting to at least 3 subsequent intravaginal encounters performed over a period of more than a month, said repeating continuing until said male exhibits an increase in the average IELT to >3 minutes, and said increase in the average IELT to >3 minutes being determined on a given day by averaging IELT of all intravaginal encounters engaged in by said male during a period of time beginning one month before the given day and extending to and including the given day.

2. The method according to claim 1, wherein the carrier is selected from the group consisting of paper, woven fabrics, and nonwoven fabrics.

3. The method according to claim 2, wherein the carrier is a non-woven fabric material comprising fibers selected from the group consisting of polyolefin, polyester, cellulose, rayon, polyamides, polyesteramide, polyvinyl alcohols, and combinations thereof.

4. The method according to claim 2, wherein the carrier is a nonwoven fabric comprising rayon and polypropylene fibers.

5. A method of inducing an increase in average intravaginal ejaculatory latency time (IELT) to >3 minutes in a male suffering premature ejaculation who at a baseline exhibits an average IELT of ≤2, said method comprising after said baseline wiping the head of the penis of said male with a wipe on a sufficient number of days over a period of more than a month as necessary to achieve said increase in average IELT to >3 minutes and as a result achieving said increase in average IELT to >3 minutes, wherein the wipe comprises a carrier and benzocaine impregnated therein.

6. The method according to claim 5, wherein the increase in average IELT achieved is to >5 minutes.

7. The method according to claim 5, wherein said wipe does not comprise any substance having an erection stimulating effect on the penis.

8. The method according to claim 6, wherein said wipe does not comprise any substance having an erection stimulating effect on the penis.

9. A method of increasing an average intravaginal ejaculatory latency time (IELT) to >3 minutes in a male whom exhibits an average IELT of ≤2 minutes on a baseline date, said method comprising a step of wiping a head of a penis of said male in advance of an intravaginal encounter with a wipe comprising a carrier and a benzocaine solution impregnated in said carrier, wherein the step of wiping the head of the penis of said male in advance of an intravaginal encounter is repeated on a sufficient number of days after said baseline date such that on a subsequent date selected 2-3 months after said baseline date the male exhibits an average IELT of >3 minutes on said subsequent date, wherein the average IELT of >3 minutes on said subsequent date is calculated by averaging IELT of all intravaginal encounters engaged in by said male during a period of time equal to one month prior to said subsequent date.

10. The method according to claim 9, wherein the step of wiping is repeated at least 3 times a week.

11. The method according to claim 9, wherein the step of wiping is repeated at least times.

12. The method according to claim 9, wherein the benzocaine solution is a 4% benzocaine solution.

13. The method according to claim 12, wherein said wipe does not comprise any substance having an erection stimulating effect on the penis.

14. The method according to claim 9, wherein the male exhibits an average IELT of >5 minutes on said subsequent date.

15. A method of increasing an average intravaginal ejaculatory latency time (IELT) to >3 minutes in a male whom exhibits an average IELT of ≤2 minutes on a baseline date, said method comprising a step of wiping a head of a penis of said male in advance of an intravaginal encounter with a wipe comprising a carrier and a 4% benzocaine solution impregnated in said carrier, and repeating the step of wiping the head of the penis of the male in advance of an intravaginal encounter on each of at least 5 different days after said baseline date such that on a subsequent date selected 2-3 months after said baseline date the male exhibits an average IELT of >3 minutes on said subsequent date, wherein the average IELT of >3 minutes on said subsequent date is calculated by averaging IELT of all intravaginal encounters engaged in by said male during a period of time equal to one month prior to said subsequent date.

* * * * *